US011192842B2

(12) United States Patent
Sun

(10) Patent No.: US 11,192,842 B2
(45) Date of Patent: Dec. 7, 2021

(54) COMPOSITIONS AND METHODS FOR THE PURIFICATION OF CFC-113 BY ADSORPTION

(71) Applicant: THE CHEMOURS COMPANY FC, LLC, Wilmington, DE (US)

(72) Inventor: Xuehui Sun, Kennett Square, PA (US)

(73) Assignee: THE CHEMOURS COMPANY FC, LLC, Wilmington, DE (US)

(*) Notice: Subject to any disclaimer, the term of this patent is extended or adjusted under 35 U.S.C. 154(b) by 0 days.

(21) Appl. No.: 17/094,894

(22) Filed: Nov. 11, 2020

(65) Prior Publication Data

US 2021/0147324 A1     May 20, 2021

Related U.S. Application Data

(60) Provisional application No. 62/937,120, filed on Nov. 18, 2019.

(51) Int. Cl.
| | | |
|---|---|---|
| *C07C 17/389* | (2006.01) | |
| *C07C 17/23* | (2006.01) | |
| *C07C 19/12* | (2006.01) | |

(52) U.S. Cl.
CPC .......... *C07C 17/389* (2013.01); *C07C 17/23* (2013.01); *C07C 19/12* (2013.01)

(58) Field of Classification Search
CPC .................................................. C07C 17/389
See application file for complete search history.

(56) References Cited

U.S. PATENT DOCUMENTS

| | | | |
|---|---|---|---|
| 6,762,333 B1 * | 7/2004 | Manzer ................ | C07C 17/00 570/123 |
| 10,696,613 B1 | 6/2020 | Nair et al. | |
| 2010/0036178 A1 | 2/2010 | Murphy et al. | |
| 2015/0094428 A1 | 4/2015 | Thenappan et al. | |

OTHER PUBLICATIONS

Adcock, J. L. et al. "Aerosol Direct Fluorination of C1 and C2 Chlorocarbons" Ind. Eng. Chem. Res. 1989, 28, 1547-1549 (Year: 1989).*

* cited by examiner

*Primary Examiner* — Medhanit W Bahta

(57) ABSTRACT

A method of separating 1,1,2-trichloro-1,2,2-trifluoroethane (CFC-113) and 1,1,1-trichloro-2,2,2-trifluoroethane (CFC-113a) includes providing an untreated composition including 1,1,2-trichloro-1,2,2-trifluoroethane (CFC-113) and 1,1,1-trichloro-2,2,2-trifluoroethane (CFC-113a). The untreated composition is treated with an adsorbent to form a treated composition in which the concentration of 1,1,1-trichloro-2,2,2-trifluoroethane (CFC-113a) is less than 93 percent of the concentration of the 1,1,1-trichloro-2,2,2-trifluoroethane (CFC-113a) in the untreated composition based on a treatment time of 24 hours.

15 Claims, No Drawings

COMPOSITIONS AND METHODS FOR THE PURIFICATION OF CFC-113 BY ADSORPTION

This Application claims the benefit of U.S. Application No. 62/937,120, filed on Nov. 18, 2019. The disclosure of 62/937,120 is hereby incorporated by reference.

FIELD

The present invention is directed to a method for the separation of CFC-113 and CFC-113a.

BACKGROUND

Compositions used as refrigerants desirably exhibit similar properties at both the evaporator and compressor of a refrigeration system. One technique to achieve uniform properties is to use a single material as the refrigerant, However, the synthesis of refrigerants often results in mixtures of isomers. The synthesis of 1,1,2-trichloro-1,2,2-trifluoroethane (CFC-113) also results in the formation of the structural isomer 1,1,1-trichloro-2,2,2-trifluoroethane (CFC-113a). In many conventional synthesis schemes structural isomers are separated by distillation based on differences in their boiling points. In the case of (CFC-113) and (CFC-113a), the boiling points of the compounds differ by only 1.3 degrees Celsius making separation by distillation difficult.

1,1,2-trichloro-1,2,2-trifluoroethane (CFC-113) may additionally be used as a precursor in the synthesis of chlorotrifluoroethylene (CTFE) by reaction with hydrogen ($H_2$) or various metals, such as zinc. If 1,1,1-trichloro-2,2,2-trifluoroethane (CFC-113a) is also present in the reaction it will be converted into 1,1-Dichloro-2,2-difluoroethylene (CFC-1112a) and 2-Chloro-1,1-difluoroethylene (CFC-1122), which are undesirable in combination with chlorotrifluoroethylene (CTFE). 1,1-Dichloro-2,2-difluoroethylene (CFC-1112a) and 2-Chloro-1,1-difluoroethylene (CFC-1122) are difficult to separate from chlorotrifluoroethylene (CTFE) by distillation.

It would be desirable in the art to have an easier and more efficient method of separation of (CFC-113) and (CFC-113a).

SUMMARY

In an exemplary embodiment, a method of separating 1,1,2-trichloro-1,2,2-trifluoroethane (CFC-113) and 1,1,1-trichloro-2,2,2-trifluoroethane (CFC-113a) includes providing an untreated composition including 1,1,2-trichloro-1,2,2-trifluoroethane (CFC-113) and 1,1,1-trichloro-2,2,2-trifluoroethane (CFC-113a). The method further includes contacting the untreated composition with a selective adsorbent to preferentially adsorb 1,1,1-trichloro-2,2,2-trifluoroethane (CFC-113a) to form a treated composition. The concentration of 1,1,1-trichloro-2,2,2-trifluoroethane (CFC-113a) in the treated composition is reduced by more than 7 percent based on the concentration of the 1,1,1-trichloro-2,2,2-trifluoroethane (CFC-113a) in the untreated composition for a contact time of 24 hours.

In another exemplary embodiment, a method of separating 1,1,2-trichloro-1,2,2-trifluoroethane (CFC-113) and 1,1,1-trichloro-2,2,2-trifluoroethane (CFC-113a) includes providing an untreated composition including 1,1,2-trichloro-1,2,2-trifluoroethane (CFC-113) and 1,1,1-trichloro-2,2,2-trifluoroethane (CFC-113a). The method further includes contacting the untreated composition with a selective adsorbent to preferentially adsorb 1,1,1-trichloro-2,2,2-trifluoroethane (CFC-113a) to form a treated composition. The concentration of 1,1,1-trichloro-2,2,2-trifluoroethane (CFC-113a) in the treated composition is reduced by more than 10 percent based on the concentration of the 1,1,1-trichloro-2,2,2-trifluoroethane (CFC-113a) in the untreated composition for a contact time of 1 week.

The present invention includes the following aspects and embodiments:

In one embodiment, disclosed herein are methods of separating 1,1,2-trichloro-1,2,2-trifluoroethane (CFC-113) and 1,1,1-trichloro-2,2,2-trifluoroethane (CFC-113a). The methods include providing an untreated composition including 1,1,2-trichloro-1,2,2-trifluoroethane (CFC-113) and 1,1,1-trichloro-2,2,2-trifluoroethane (CFC-113a) and contacting the untreated composition with a selective adsorbent to preferentially adsorb 1,1,1-trichloro-2,2,2-trifluoroethane (CFC-113a) to form a treated composition. The concentration of 1,1,1-trichloro-2,2,2-trifluoroethane (CFC-113a) in the treated composition is reduced by more than 7 percent based on the concentration of the 1,1,1-trichloro-2,2,2-trifluoroethane (CFC-113a).

According to any of the foregoing embodiments, also disclosed herein are methods in which the concentration of 1,1,1-trichloro-2,2,2-trifluoroethane (CFC-113a) in the treated composition is less than about 0.1 weight percent.

According to any of the foregoing embodiments, also disclosed herein are methods in which the selective adsorbent includes carbon.

According to any of the foregoing embodiments, also disclosed herein are methods in which the selective adsorbent includes nickel or copper.

According to any of the foregoing embodiments, also disclosed herein are methods which additionally include treating the selective adsorbent with hydrogen prior to contacting the untreated composition.

According to any of the foregoing embodiments, also disclosed herein are methods in which the amount of 1,1,2-trichloro-1,2,2-trifluoroethane (CFC-113) plus 1,1,1-trichloro-2,2,2-trifluoroethane (CFC-113a) in the untreated composition is at least 98 weight percent based on the total weight of the untreated composition.

According to any of the foregoing embodiments, also disclosed herein are methods in which the untreated composition is contacted with the adsorbent for a contact time of 24 hours.

According to any of the foregoing embodiments, also disclosed herein are compositions formed by any of the above methods.

In one embodiment, disclosed herein are methods of separating 1,1,2-trichloro-1,2,2-trifluoroethane (CFC-113) and 1,1,1-trichloro-2,2,2-trifluoroethane (CFC-113a). The methods include providing an untreated composition including 1,1,2-trichloro-1,2,2-trifluoroethane (CFC-113) and 1,1,1-trichloro-2,2,2-trifluoroethane (CFC-113a) and contacting the untreated composition with a selective adsorbent to preferentially adsorb 1,1,1-trichloro-2,2,2-trifluoroethane (CFC-113a) to form a treated composition. The concentration of 1,1,1-trichloro-2,2,2-trifluoroethane (CFC-113a) in the treated composition is reduced by more than about 7, more than about 8 and, in some cases, more than about 10 percent based on the concentration of the 1,1,1-trichloro-2,2,2-trifluoroethane (CFC-113a) in the untreated composition for a contact time of about 30 minutes to about 1 week.

According to any of the foregoing embodiments, also disclosed herein are methods in which the concentration of 1,1,1-trichloro-2,2,2-trifluoroethane (CFC-113a) in the treated composition is less than about 0.1 weight percent.

According to any of the foregoing embodiments, also disclosed herein are methods in which the concentration of 1,1,1-trichloro-2,2,2-trifluoroethane (CFC-113a) in the treated composition is less than 0.05 weight percent.

According to any of the foregoing embodiments, also disclosed is using the CFC-113 containing compositions of the invention in the production of CTFE.

The embodiments of the disclosure can be used alone or in combinations with each other. Other features and advantages of the present invention will be apparent from the following more detailed description of the preferred embodiment which illustrates, by way of example, the principles of the invention.

DETAILED DESCRIPTION

Provided is a method for the separation of 1,1,2-trichloro-1,2,2-trifluoroethane (CFC-113) and 1,1,1-trichloro-2,2,2-trifluoroethane (CFC-113a) by liquid phase adsorption.

The ability of an adsorbent to interact with the species of a mixture is related to the surface energy of the adsorbent. Separation via adsorption relies on differences in the interaction between the surface groups of the adsorbent and the components of the contacting composition.

1,1,2-trichloro-1,2,2-trifluoroethane (CFC-113) and 1,1,1-trichloro-2,2,2-trifluoroethane (CFC-113a) have the same chemical formula and are structural isomers of one another. Mixtures of 1,1,2-trichloro-1,2,2-trifluoroethane (CFC-113) and 1,1,1-trichloro-2,2,2-trifluoroethane (CFC-113a) may be separated by the partitioning of 1,1,1-trichloro-2,2,2-trifluoroethane (CFC-113a) onto a selective adsorbent while the 1,1,2-trichloro-1,2,2-trifluoroethane (CFC-113) remains as a mobile liquid phase. The ability of a selective adsorbent to bond to the (CFC-113a) of a (CFC-113)/(CFC-113a) mixture is dependent on the materials and surface groups of the surface of the adsorbent.

In some embodiments, selective adsorbent treatments reduce the concentration of 1,1,1-trichloro-2,2,2-trifluoroethane (CFC-113a) in a 1,1,2-trichloro-1,2,2-trifluoroethane (CFC-113)/1,1,1-trichloro-2,2,2-trifluoroethane (CFC-113a) mixture by at least 7 percent based on the concentration of the (CFC-113a) prior to treatment.

In some embodiments, the weight ratio of the selective adsorbent to the 1,1,2-trichloro-1,2,2-trifluoroethane (CFC-113)/1,1,1-trichloro-2,2,2-trifluoroethane (CFC-113a) untreated composition is at least 1:30, at least 1:25, at least 1:20, at least 1:15, at least 1:10, at least 1:5, at least 1:3, at least 1:2, less than 1:1, and combinations and sub-combinations thereof.

In some embodiments, the temperature for the selective adsorption is greater than about 0 to about 45° C. (degrees Celsius), about 5 to 40° C. and in some cases about 10 to 35° C.

In some embodiments, the pressure employed for the selective adsorption can vary and is normally atmospheric and, in some cases, sub-atmospheric to atmospheric pressure.

In some embodiments, the surface of the adsorbent may include metals. In some embodiments, the surface of the adsorbent may include transition metals. In some embodiments, the surface of the adsorbent may include nickel or copper. In some embodiments, the adsorbent may include activated carbon. In some embodiments, the adsorbent may include nickel on carbon (Ni/C) or copper on carbon (Cu/C).

The amount of the metal loading can range from about 2 to about 25, about 5 to 20 and, in some cases, about 10 to 15 wt. % of the adsorbent The surface of the adsorbent may be treated to impart additional functional groups to the surface of the adsorbent. In some embodiments, the surface treatment may include exposure to hydrogen ($H_2$). In some embodiments, activated carbon may be dried at elevated temperature under a nitrogen ($N_2$) atmosphere. In some embodiments, the surface treatment may be performed at elevated temperature. In some embodiments, the surface treatment may be performed at a temperature of at least 100° C., at least 150° C., at least 200° C., at least 250° C., less than 350° C., less than 300° C., less than 260° C., and combinations and subranges thereof. The surface treatment may be performed prior to the initial contact between the adsorbent and a composition. Surface treatments may also be performed during the regeneration of the adsorbent. In some embodiments, the adsorbent is subjected to a surface treatment prior to initial use and during regeneration of the adsorbent.

The particle size of the adsorbent can range from about 4 to about 20 mesh, about 6 to about 16, and in some cases about 7 to about 14 mesh. The surface area and pore size of the adsorbent particles can be tailored using conventional methods known in the adsorbent art.

In some embodiments, the treatment of an untreated composition of 1,1,2-trichloro-1,2,2-trifluoroethane (CFC-113) and 1,1,1-trichloro-2,2,2-trifluoroethane (CFC-113a) may reduce the concentration of the (CFC-113a) in the treated composition to less than 93 percent, less than 90 percent, less than 80 percent, less than 70 percent, less than 60 percent, less than 50 percent, less than 40 percent, less than 30 percent, less than 20 percent, or less than 10 percent of the concentration of the 1,1,1-trichloro-2,2,2-trifluoroethane (CFC-113a) in the untreated composition based on a contact time of about 30 minutes.

In some embodiments, the treatment of an untreated composition of 1,1,2-trichloro-1,2,2-trifluoroethane (CFC-113) and 1,1,1-trichloro-2,2,2-trifluoroethane (CFC-113a) may reduce the concentration of the (CFC-113a) in the treated composition to less than 93 percent, less than 90 percent, less than 80 percent, less than 70 percent, less than 60 percent, less than 50 percent, less than 40 percent, less than 30 percent, less than 20 percent, less than 10 percent, or less than 7 percent of the concentration of the 1,1,1-trichloro-2,2,2-trifluoroethane (CFC-113a) in the untreated composition based on a contact time of one week.

In some embodiments, the concentration of (CFC-113a) in the treated composition may be reduced to less than 0.10 weight percent, less than 0.05 weight percent, 0.01 weight percent, and subranges thereof based on the total amount of (CFC-113) and (CFC-113a) in the untreated composition.

The treatment of the untreated composition may be performed as a batch or continuous process. In some embodiments, the untreated composition may be contacted with the adsorbent in a batch process. In one embodiment, the batch process is performed in a glass or metal lined reaction vessel.

In some embodiments, the treatment of the untreated composition may be performed as a continuous process. In some embodiments, the untreated composition may be contacted with the adsorbent in a fluidized bed reactor. In some embodiments, the untreated composition may be contacted with the adsorbent in a fixed bed reactor.

In some embodiments, the contact time for removing CFC-113a from a CFC-113 containing composition can range from about 30 minutes to about 1 week, about 60 minutes to about 4 days and, in some cases about 90 minutes to about 1 day.

The CFC-113 containing compositions produced by the instant invention can be used as a precursor for producing CTFE. Examples of methods for converting the inventive CFC-113 into CTFE are disclosed by US 20100036178 A1 (e.g., converting 113 to CTFE by reacting with reactive metal such as Zn) and U.S. Pat. No. 10,696,613 B1 (e.g., gas phase dichlorination of 113 to CTFE by H2 with present of a catalyst). The resultant CTFE containing compositions can be converted into a copolymer, for example, using the methods disclosed in US 20150094428 A1 (e.g., using CTFE as monomer to make a copolymer). The disclosure of the foregoing patents and patent applications are hereby incorporated by reference.

The following Examples are provided to illustrate certain embodiments of the invention and shall not limit the scope of the appended claims.

EXAMPLES

General procedure for liquid phase adsorption of (CFC-113a) from (CFC-113) for Examples 1-7.

The molecular sieves 13X, BPL carbon, and dried Calgon Sulfusorb were dried at 250° C. overnight before use. $H_2$ activated Calgon SULFUSORB and BASF E474 TR (Ru, ⅛" pellets) were treated with $H_2$ at 250° C. three hours before use.

The CFC-113 starting material was dried with 3 angstrom molecular sieves before use. The CFC-113 starting material was mixed with adsorbent in a glass bottle at room temperature. The glass bottle was sealed with a cap and shaken for about 5 minutes. The shaken mixture was allowed to sit at room temperature for a period time as specified in Table 1 below. The resulting material was analyzed using a gas chromatograph (GC) with a flame ionization detector (FID). The concentration of CFC-113a in the starting and treated materials is shown below in Table 1.

TABLE 1

| Test | | adsorbent/113 weight ratio (g/g) | Contact time | 113a GC FID area % | 113a reduction (%) |
|---|---|---|---|---|---|
| | Starting material | | | 0.1229% | |
| 1 Comparative | molecular sieve 13X | 1/20 | 24 hours | 0.1235% | (0.49) |
| 2 Comparative | Dried Calgon SULFUSORB ® | 1/20 | 24 hours | 0.1229% | 0 |
| 3 Inventive | $H_2$ activated Calgon SULFUSORB ® | 1/5 | 4 hours | 0.1069% | 13.02 |
| | | | 24 hours | 0.0499% | 81.20 |
| | | | one week | 0.0085% | 93.08 |
| 4 Inventive | $H_2$ activated Calgon SULFUSORB ® | 1/20 | 24 hours | 0.1169% | 4.88 |
| | | | one week | 0.1101% | 10.41 |
| 5 Inventive | $H_2$ activated E474TR (Ru) | 1/3 | 24 hours | 0.0099% | 91.94 |
| 6 Inventive | $H_2$ activated E474TR (Ru) | 1/20 | 24 hours | 0.1121% | 8.79 |
| | | | one week | 0.0926% | 24.65 |
| 7 Comparative | BPL carbon | 1/20 | 24 hours | 0.1143% | 7.00 |

In the above inventive examples, the treatment of a composition including both (CFC-113) and (CFC-113a) resulted in the reduction of the concentration of (CFC-113a) in the resulting treated sample. The pretreatment of a microporous metal adsorbent, such as the nickel of the SULFUSORB®, with a reductive atmosphere resulted in improved selectivity of the adsorbent to (CFC-113a).

Additionally, in the above examples, increased loading of the adsorbent resulted in an increase in the resulting reduction of the (CFC-113a) concentration by a factor greater than the weight ratio change.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of separating 1,1,2-trichloro-1,2,2-trifluoroethane (CFC-113) and 1,1,1-trichloro-2,2,2-trifluoroethane (CFC-113a) comprising:

providing a composition including 1,1,2-trichloro-1,2,2-trifluoroethane (CFC-113) and 1,1,1-trichloro-2,2,2-trifluoroethane (CFC-113a);

contacting the composition with an adsorbent comprising carbon to adsorb 1,1,1-trichloro-2,2,2-trifluoroethane (CFC-113a) to form a treated composition;

wherein the concentration of 1,1,1-trichloro-2,2,2-trifluoroethane (CFC-113a) in the treated composition is reduced.

2. The method of claim 1:

wherein the concentration of 1,1,1-trichloro-2,2,2-trifluoroethane (CFC-113a) in the treated composition is less than 0.1 weight percent.

3. The method of claim 2:

wherein the concentration of 1,1,1-trichloro-2,2,2-trifluoroethane (CFC-113a) in the treated composition is less than 0.05 weight percent.

4. The method of claim 1:
wherein the selective adsorbent includes nickel or copper.

5. The method of claim 1:
further comprising treating the adsorbent with hydrogen; wherein the adsorbent is treated with hydrogen prior to contacting the composition.

6. The method of claim 1:
wherein the amount of 1,1,2-trichloro-1,2,2-trifluoroethane (CFC-113) plus 1,1,1-trichloro-2,2,2-trifluoroethane (CFC-113a) in the composition is at least 98 weight percent based on the total weight of the untreated composition.

7. The method of claim 1:
wherein the composition is contacted with the adsorbent for a contact time of at least 30 minutes.

8. A method of separating 1,1,2-trichloro-1,2,2-trifluoroethane (CFC-113) and 1,1,1-trichloro-2,2,2-trifluoroethane (CFC-113a) comprising:
providing a composition including 1,1,2-trichloro-1,2,2-trifluoroethane (CFC-113) and 1,1,1-trichloro-2,2,2-trifluoroethane (CFC-113a);
contacting the composition with an adsorbent comprising carbon to adsorb 1,1,1-trichloro-2,2,2-trifluoroethane (CFC-113a) to form a treated composition;
wherein the adsorbent is surface treated to impart additional functional groups to the surface of the adsorbent;
wherein the concentration of 1,1,1-trichloro-2,2,2-trifluoroethane (CFC-113a) in the treated composition is reduced by more than 10 percent based on the concentration of the 1,1,1-trichloro-2,2,2-trifluoroethane (CFC-113a).

9. The method of claim 8:
wherein the concentration of 1,1,1-trichloro-2,2,2-trifluoroethane (CFC-113a) in the treated composition is less than about 0.1 weight percent.

10. The method of claim 9:
wherein the concentration of 1,1,1-trichloro-2,2,2-trifluoroethane (CFC-113a) in the treated composition is less than about 0.05 weight percent.

11. The method of claim 1 wherein the adsorbent has a particle size ranging from about 4 to about 20 mesh.

12. The method of claim 1 further comprises recovering CFC-113 and converting the recovered CFC-113 into CTFE.

13. A method for purifying a composition comprising 1,1,2-trichloro-1,2,2-trifluoroethane (CFC-113) and 1,1,1-trichloro-2,2,2-trifluoroethane (CFC-113a), the method comprising:
providing a composition including 1,1,2-trichloro-1,2,2-trifluoroethane (CFC-113) and 1,1,1-trichloro-2,2,2-trifluoroethane (CFC-113a);
contacting the composition with carbon under conditions sufficient to adsorb 1,1,1-trichloro-2,2,2-trifluoroethane (CFC-113a) to form a treated composition;
wherein the carbon is treated before the contacting; and,
wherein the concentration of 1,1,1-trichloro-2,2,2-trifluoroethane (CFC-113a) in the treated composition is reduced.

14. The method of claim 13 wherein the adsorbent is treated with hydrogen.

15. The method of claim 13 wherein the adsorbent is treated with at least one metal.

* * * * *